(12) United States Patent
Bachar et al.

(10) Patent No.: US 9,775,594 B2
(45) Date of Patent: Oct. 3, 2017

(54) LAPAROSCOPIC SEAL BRIDGE

(71) Applicants: EON SURGICAL LTD., Tel-Aviv (IL); KIPA AB, Helsingborg (SE)

(72) Inventors: Yehuda Bachar, Givat Shmuel (IL); Danny Farin, Hod Ha'Sharon (IL)

(73) Assignee: EON SURGICAL LTD., Tel-Aviv (IL)

( * ) Notice: Subject to any disclaimer, the term of this patent is extended or adjusted under 35 U.S.C. 154(b) by 471 days.

(21) Appl. No.: 14/368,175

(22) PCT Filed: Dec. 21, 2012

(86) PCT No.: PCT/EP2012/076857
§ 371 (c)(1),
(2) Date: Jun. 23, 2014

(87) PCT Pub. No.: WO2013/093107
PCT Pub. Date: Jun. 27, 2013

(65) Prior Publication Data
US 2014/0343365 A1    Nov. 20, 2014

Related U.S. Application Data

(60) Provisional application No. 61/579,670, filed on Dec. 23, 2011.

(51) Int. Cl.
*A61B 17/02* (2006.01)
*A61B 17/34* (2006.01)

(52) U.S. Cl.
CPC ...... *A61B 17/0218* (2013.01); *A61B 17/3421* (2013.01); *A61B 17/3462* (2013.01); *A61B 2017/3419* (2013.01); *A61B 2017/3441* (2013.01); *A61B 2017/3464* (2013.01)

(58) Field of Classification Search
CPC ............ A61B 17/0218; A61B 17/3421; A61B 17/3462; A61B 2017/3419; A61B 2017/3464; A61B 2017/3441
See application file for complete search history.

(56) References Cited

U.S. PATENT DOCUMENTS

| | | |
|---|---|---|
| 5,176,653 A | 1/1993 | Metals |
| 5,375,588 A | 12/1994 | Yoon |
| 5,392,766 A | 2/1995 | Masterson et al. |
| 6,146,402 A | 11/2000 | Munoz |

(Continued)

FOREIGN PATENT DOCUMENTS

| | | |
|---|---|---|
| WO | 2011128392 A1 | 10/2011 |
| WO | 2012035524 A2 | 3/2012 |

*Primary Examiner* — Ellen C Hammond
(74) *Attorney, Agent, or Firm* — Baker and Hostetler LLP

(57) ABSTRACT

A system and method for passing an end portion of a needle system from a body cavity to an outer environment through a laparoscopic port is provided. The system comprises a seal bridge which comprises an elongated body. The seal bridge is telescopically introducible at a first proximal end, through a first lumen in the port and bypassing a seal mechanism of the laparoscopic port. The seal bridge is adapted to be inserted through the proximal opening port to be deployed in the lumen of the port and thereby bridging across and/or deactivating the seal of the port. The method comprises positioning a distal portion of a needle shaft from within the body cavity into the port lumen and across the seal opened by the seal bridge.

10 Claims, 3 Drawing Sheets

(56) References Cited

U.S. PATENT DOCUMENTS

| | | | | |
|---|---|---|---|---|
| 6,165,184 | A * | 12/2000 | Verdura | A61B 17/34 606/148 |
| 7,828,775 | B2 * | 11/2010 | Okoniewski | A61B 17/3421 604/167.01 |
| 2005/0234294 | A1 | 10/2005 | Saadat et al. | |
| 2007/0073323 | A1 | 3/2007 | Carter et al. | |
| 2009/0099478 | A1 * | 4/2009 | Cassells | A61B 5/411 600/583 |
| 2010/0274093 | A1 * | 10/2010 | Shelton, IV | A61B 17/3423 600/206 |
| 2011/0046449 | A1 | 2/2011 | Minnelli et al. | |
| 2011/0166595 | A1 * | 7/2011 | Vidlund | A61B 17/0057 606/213 |
| 2011/0208007 | A1 * | 8/2011 | Shohat | A61B 17/3403 600/227 |
| 2012/0083826 | A1 * | 4/2012 | Chao | A61B 17/00234 606/205 |
| 2014/0005474 | A1 * | 1/2014 | Farin | A61B 1/00154 600/104 |

* cited by examiner

LAPAROSCOPIC SEAL BRIDGE

CROSS-REFERENCE TO RELATED APPLICATIONS

This application is a National Stage of International patent application PCT/EP2012/076857, filed on Dec. 21, 2012, which claims priority to U.S. provisional patent application No. 61/579,670, filed on Dec. 23, 2011, the disclosures of which are incorporated by reference in their entirety.

FIELD OF THE INVENTION

The present invention generally relates to systems and methods for performing surgeries, and more specifically to methods and devices for micro-laparoscopic surgeries.

BACKGROUND OF THE INVENTION

Laparoscopic or minimally invasive surgery includes the use of several relatively small ports into the abdomen by which different types of instrumentation and accessories are introduced and used for different surgical interventions (usually performed under endoscopic vision). Although usually considered superior in several aspects to open surgery, the use of a plurality of 5 to 15 mm ports still leads to local pain, scars, and possibly port related complications such as hernia in scars and the need for one or two assistants in addition to the surgeon.

In past years, new versions of laparoscopic systems and approaches were introduced to overcome several of the "classic" laparoscopy disadvantages, mainly the Single-Port Access (SPA) and the Needlescopy approaches. In SPA the surgeon operates almost exclusively through a single entry point, typically through the patient's navel, using access ports and hand instrument. Highly experienced and skilled physicians may still use standard laparoscopic hand instruments, although the use of a single port access decreases its triangulation and complicates maneuverability. The use of special-purpose articulating instrumentation was introduced to overcome this difficulty, although it is considered very expensive, necessitates special training and still involves complex surgical maneuverability.

"Minilaparoscopy" (also known as "needelscopic laparoscopy") is intended to overcome the problems encountered in single port access surgery. While the advantages of SPA include improved cosmetic, less abdominal wall pain and less incision related complications, this surgical approach has disadvantages. The vision is partially obscured by the paralleled inserted instruments; there is minimal triangulation and limited maneuverability of the surgical instruments. Minilaparoscopy maintains the same mode of surgery as standard laparoscopy however there is only one sheath and all the rest of the instruments are connected to needle-like shafts which are inserted with no trocar and therefore provide comparable cosmetic and painless results as SPA.

In needlescopy, the laparoscopic ports are replaced with small incisions, usually between 2 to 3 mm in diameter. The surgery is performed by inserting narrow guide tubes into the small incisions and then passing tiny instruments through the tubes, while using a small camera for guidance. The small instruments have very slender tips which make dissection and tissue maneuvering very difficult. Furthermore the instrument tips may have a greater tendency to break and their removal may be cumbersome and difficult.

In order to avoid such difficulties while maintaining small incision porting, it has been advised to combine the single-port and the needlescopic approaches. This is achieved by first inserting regular-sized interchangeable end-effectors through a regular size single port access and then detachably attaching them to corresponding distal portions of needle-sized manipulators. The manipulators are protruding into abdomen cavity via miniature needlescopic type incisions. Locating and engaging between a needle manipulator and an end-effector inside the abdominal cavity may be risky and cumbersome, therefore the Inventors suggest that such engagement and connection will take place in a more secured location such as outside the abdominal cavity or even outside patient's body.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing devices and methods according to the appended patent claims.

According to a first aspect, a system for passing an end portion of a needle system from a body cavity to an outer environment through a laparoscopic port is provided. The system comprises an elongated sleeve which comprises a second proximal opening, a second distal opening, a second lumen extending between the second proximal opening and the second distal opening, and a seal provided in the second lumen. The system further comprises a seal bridge which comprises an elongated body. The elongated sleeve is telescopically introducible at a first proximal end, through a first lumen and bypassing a seal mechanism of the laparoscopic port. The seal bridge is adapted to be inserted through the second proximal opening to be deployed in the second lumen and thereby bridging across and/or deactivating the seal of the elongated sleeve.

Deactivating means, in the context of the application, affecting the seal to be open to end portion as well as fluids etc passing therethrough.

Some examples of the system comprise a laparoscopic port.

In some examples of the system, the elongated body of the seal bridge comprises a third distal opening, a sealed proximal end and a third lumen extending at least partially therebetween.

In some examples of the system, the seal bridge is sealed to gas.

In some examples of the system, the elongated body has a proximal segment and distal segment, the proximal segment has a larger outer diameter than the distal segment.

In some examples of the system, the third lumen is adapted to receive the end portion of the needle when the needle entering the second distal opening.

In some examples of the system, the second proximal opening is provided with a removable sealing covering.

In some examples of the system, the seal comprises a zero seal.

In some examples of the system, the seal comprises an instruments seal.

In some examples of the system, the third distal opening third distal opening has a beveled opening.

According to a further aspect a method for passing an end portion of a needle system from a body cavity to an outer environment is disclosed. The method comprises telescopically introducing an elongated sleeve in a lumen of a laparoscopic port through a first proximal opening, thereby bypassing a seal mechanism of the laparoscopic port. The method further comprises bridging across and/or deactivating a seal in the second lumen by inserting a seal bridge into a second lumen of the elongated sleeve, through a second proximal opening of the elongated sleeve and passing the end portion of the needle system into the second lumen via a second distal opening of the elongated sleeve. Moreover the method comprises positioning a portion of the needle across the seal, and removing the seal bridge.

In some examples, the method comprises positioning the portion of the needle across the seal by positioning the end portion of the needle system through a third distal opening of the seal bridge and into a third lumen of the seal bridge.

In some examples, the method comprises creating a beveled entry passage at the third opening, after deployment in said second lumen.

In some examples, the method comprises positioning the portion of the needle across the seal by a pushing force provided by the needle on a distal end portion of the seal bridge.

In some examples, the method comprises removing a removable sealing covering from the second proximal opening of the elongated sleeve before inserting the seal bridge into the second lumen.

In some examples, the method comprises extending the elongated sleeve to a chosen position adjacent the end portion of the needle.

In some examples, the method comprises maintaining the second lumen sealed to gas after bridging across and/or deactivating the seal.

In some examples, the method comprises progressing the seal bridge until bridging across and/or deactivating the seal.

According to a further aspect, a seal bridge for a laparoscopic port system is provided. The seal bridge comprises an elongated body adapted to be deployed in a lumen of an inter-sleeve and bridging across and/or deactivating a seal of the inter-sleeve.

In some examples of the seal bridge, the elongated body comprises a distal opening, a sealed proximal end and a lumen extending at least partially therebetween.

In some examples of the seal bridge, the elongated body has a proximal segment and distal segment, the proximal segment has a larger outer diameter than the distal segment.

In some examples of the seal bridge, the lumen is adapted to receive an end portion of a needle when the needle entering the distal opening.

In some examples of the seal bridge, the distal opening has a beveled opening.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTIONS OF EXEMPLARY EMBODIMENTS

The present invention generally relates to systems and methods for performing surgeries, and more specifically to methods and devices for micro-laparoscopic surgeries.

Figure 1:
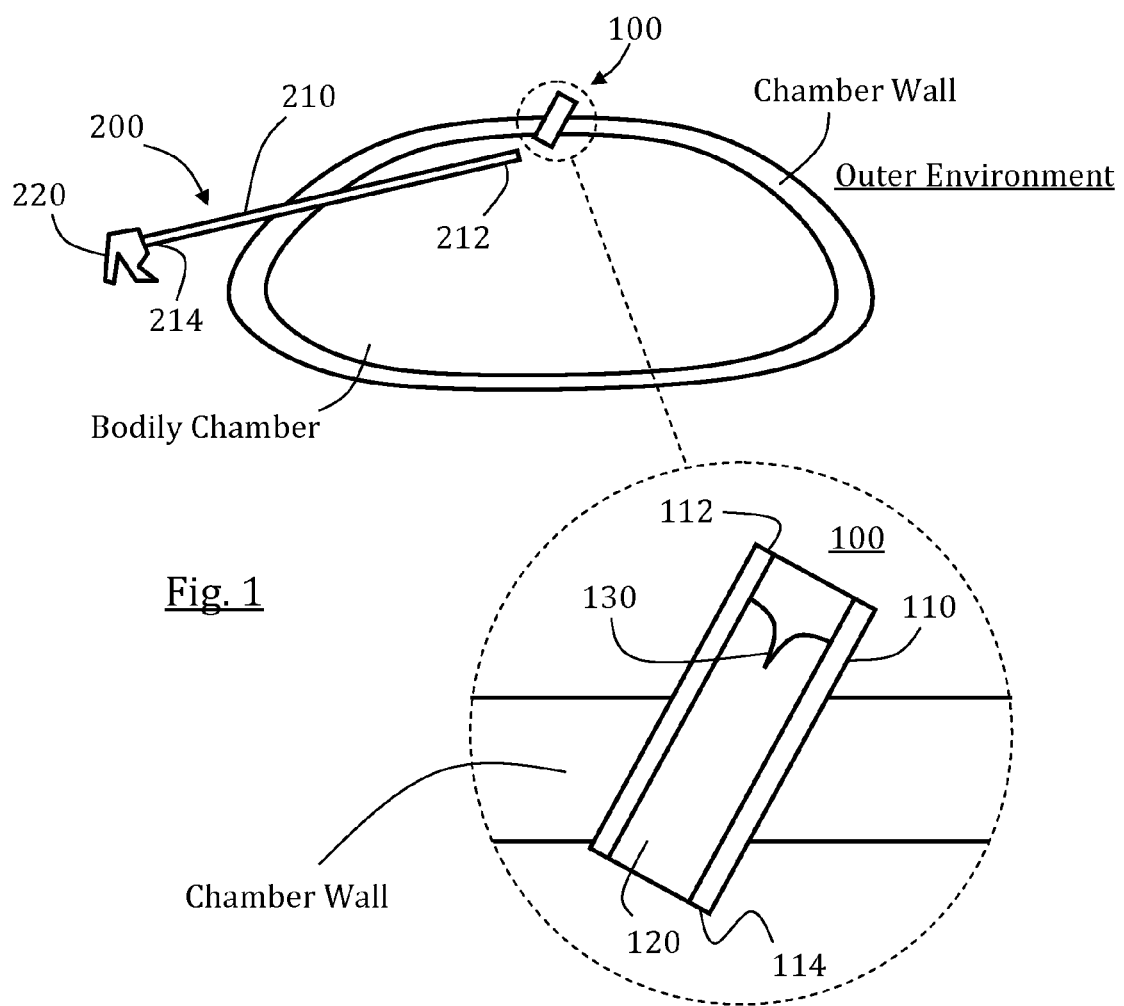
FIG. 1 schematically illustrates a cut view and an enlarged partial view of a laparoscopic port provided between a bodily cavity and an outer environment, adjacent a needle end portion, in accordance with an exemplary embodiment of the present invention.

In an aspect of some embodiments, there is provided a system for performing laparoscopic surgeries that is configured for creating a contained passage therethrough for a needle distal end from a body cavity to an outer environment. In some embodiments of the invention, the system includes a laparoscopic port having a lumen deployable between a body cavity and an outer environment. Reference is made to FIG. 1 which schematically illustrates a cut view and an enlarged partial view of a laparoscopic port 100 provided in or through a chamber wall between a bodily cavity or chamber and an outer environment, adjacent an end portion 212 of a needle system 200, in accordance with an exemplary embodiment of the present invention. The body cavity may be though not limited to an abdominal cavity; the outer environment may be though not limited to an outpatient environment, for example an operating room environment. Needle system 200 may be a manually operable system for connecting with and/or operating a detachable end effector or surgical head (not shown), and may be percutaneously or introducible via a small incision or a trocar system (not shown). Needle system 200 includes an elongated shaft 210 ending with end portion 212 and comprising a proximal portion 214 connected with a handle 220. Laparoscopic port 100 includes a body 110 having a proximal end 112, a distal end 114 and a lumen 120 provided along its length and opened at both sides on ends 112 and 114. Laparoscopic port 100 also includes a seal mechanism 130 provided in lumen 120 for preventing migration of inflation gas from body chamber to outer environment. Seal mechanism 130 may be any known and/or commercially available gas sealing combination or device, and may include a single or a plurality of seals, valves and/or membranes, for example a zero seal and/or an instrument seal.

In some embodiments, the system does not include a laparoscopic port but is intended for insertion through and/or connection with such, for example a commercially available sheath, trocar and/or port intended for laparoscopy.

In some embodiments of the invention, the system includes an elongated sleeve 300 (shown in FIG. 2B) which is telescopically introducible by an elongated sleeve body 310, optionally selectively to surgeon's choice, through laparoscopic port lumen 120 thereby bypassing through seal mechanism 130. This way seal mechanism 130 is being forced to open and accommodate traveling therethrough of artifacts at different sizes (e.g., needle end portion 212 with or without a surgical head connected thereto) while avoiding damage to its parts or members (e.g., seals or membranes) and/or hindering the artifact. In some embodiments of the invention, elongated sleeve 300 is extendable to a predetermined location in the body cavity, thereby creating a contained passage from the predetermined location to the outer environment. Exemplary port bypassing sleeves or guiding cannulas are disclosed in International Patent application number PCT/IB2011/054102 filed Sep. 19, 2011 and titled "Micro Laparoscopy Devices and Deployments thereof", the disclosures of which is fully incorporated herein by reference.

In some embodiments of the invention, elongated sleeve 300 includes a proximal opening 312 at a proximal end of elongated sleeve body 310 (optionally provided with a removable sealing covering 340), a distal opening 314 at a distal end of elongated sleeve body 310 and a lumen 320 extending therebetween, opened at both ends. In order to prevent gas migration at deployment in the laparoscopic port, the elongated sleeve includes at least one seal 330 provided in its lumen. In some embodiments of the invention, the at least one seal 330 includes a zero seal that is adapted to prevent gas migration at absence of a surgical instrument provided therethrough and/or an instrument seal that is adapted to prevent gas migration when an instrument (optionally in a diameter for example between 1 to 12 mm) is provided therethrough.

In order to prevent potential damage and/or sticking of a sharp instrument end and/or a needle with sleeve seal 330 (especially but not limited to a zero type seal), a seal bridge 500 (shown in FIG. 2C) may be selectively deployable in elongated sleeve lumen 320. Seal bridge 500 may include an extension, referred to as elongated body 510, a sealed proximal end portion 512 and a seal bridge distal end portion 514. In some optional embodiments, elongated body 510 is segmented to at least two segments along its length that are differentiated by shape and/or size, for example proximal segment 516 and distal segment 518. In some embodiments, proximal segment 516 is sized and/or shaped to snugly fit in sleeve lumen 320, whereas distal segment 518 is sized and/or shaped to pass through and open sleeve seal 330, optionally in a centralized and/or homogenous fashion while avoiding any damage associated with size and/or orientation related circumstances. In some embodiments of the invention, seal bridge 500 is configured for bridging across and/or deactivating sleeve seal 330 when deployed, thereby facilitating unhindered passage for a needle or other artifact while preventing such damage and/or sticking to the seal. In some embodiments, seal bridge 500 is configured for bridging across all seals in a sleeve, optionally a distal-most seal, optionally a zero seal.

In some exemplary embodiments of the invention, seal bridge 500 is sealed to gas so that when deployed in elongated sleeve lumen 320, while bridging across and/or deactivating the sleeve seal(s) 330, no gas can escape from the body cavity and the outer environment. Optionally, additionally or alternatively, the seal bridge includes a removable cover and/or a selectively operable seal (not shown).

In some embodiments of the invention, the at least one sleeve seal 330 is positioned at a fixed length distal to proximal opening 312. The fixed length may be any length, for example 1 to 25 cm, optionally 5 cm distal to elongated sleeve proximal opening 312. In some embodiments of the invention, elongated body 510 is extendable in sleeve lumen 320 from proximal opening 312 and over the fixed length, thereby forcing seal 330 to open. Optionally, distal end portion 514 outer diameter is sized and/or shaped to fit in sleeve lumen 320 and divert seal 330.

Additionally and/or alternatively, in order to prevent potential damage and/or sticking of a sharp instrument end and/or a needle with sleeve seal 330 (especially but not limited to a zero type seal), a seal bridge 400 (shown in FIG. 2D) may be selectively deployable in elongated sleeve lumen 320. Seal bridge 400 may include an extension, at least partially hollow, referred to as elongated body 410, a sealed proximal end portion 412, an opened distal end 414 and a lumen 420 provided partially along seal bridge 400 length and communicating with opening at distal end 414. In some optional embodiments, elongated body 410 is segmented to at least two segments along its length that are differentiated by shape and/or size, for example proximal segment 416 and distal segment 418. In some embodiments, proximal segment 416 is sized and/or shaped to snugly fit in sleeve lumen 320, whereas distal segment 418 is sized and/or shaped to pass through and open sleeve seal 330, optionally in a centralized and/or homogenous fashion while avoiding any damage associated with size and/or orientation related circumstances. In some embodiments of the invention, seal bridge 400 is configured for bridging across and/or deactivating sleeve seal 330 when deployed, thereby facilitating unhindered passage for a needle or other artifact while preventing such damage and/or sticking to the seal. In some embodiments, seal bridge 400 is configured for bridging across all seals in a sleeve, optionally a distal-most seal, optionally a zero seal.

In some exemplary embodiments of the invention, seal bridge 400 is sealed to gas so that when deployed in elongated sleeve lumen 320, while bridging across and/or deactivating the sleeve seal(s) 330, no gas can escape from the body cavity and the outer environment. Optionally, additionally or alternatively, the seal bridge includes a removable cover and/or a selectively operable seal (not shown).

In some embodiments of the invention, the at least one sleeve seal 330 is positioned at a fixed length distal to proximal opening 312. The fixed length may be any length, for example 1 to 25 cm, optionally 5 cm distal to elongated sleeve proximal opening 312. In some embodiments of the invention, hollow extension or elongated body 410 is extendable in sleeve lumen 320 from proximal opening 312 and over the fixed length, thereby forcing seal 330 to open. Optionally, distal end 414 outer diameter is sized and/or shaped to fit in sleeve lumen 320 and divert seal 330.

Figure 2A:
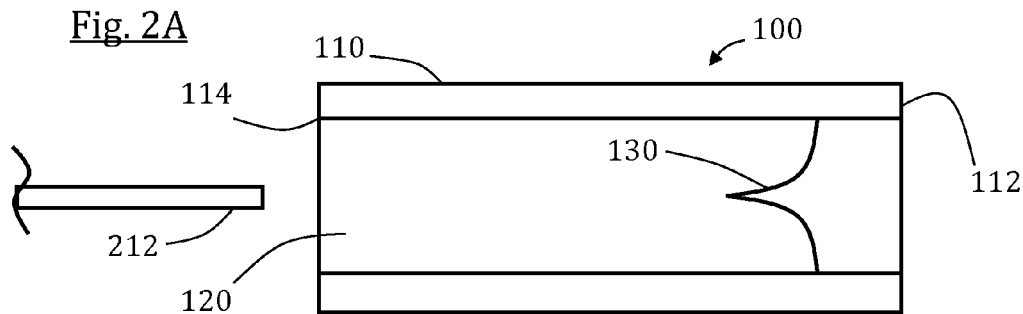
FIGS. 2A-E schematically illustrate cut views showing different stages of passing a needle end portion through a laparoscopic port system, in accordance with an exemplary embodiment of the present invention.
Figure 2B:
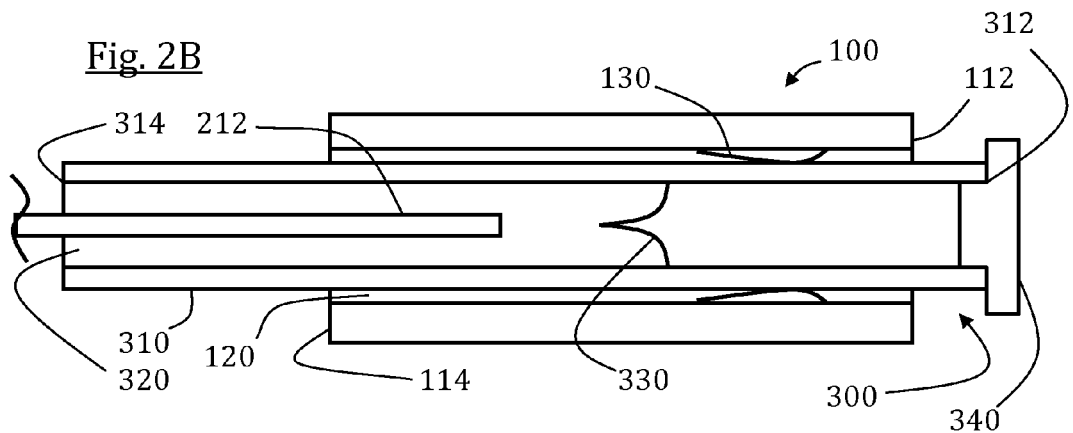
Figure 2C:
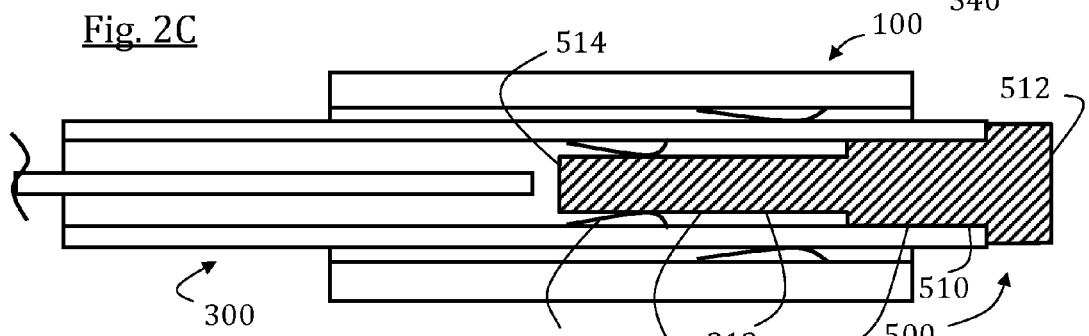

In an aspect of some embodiments, there is also provided a method for passing a needle end portion provided in a body cavity to and/or from an outer environment. Reference is made to FIGS. 2A, 2B, 2D and 2E which schematically illustrate, respectively, cut views showing different stages of passing a needle end portion 212 through laparoscopic port system 100, in accordance with an exemplary embodiment of the present invention. In some embodiments laparoscopic port 100 is first deployed to create a normally closed passage (with the normally closed sealing mechanism 130 or with other means) between body cavity or chamber and outer environment (as shown previously in FIG. 1). As shown in FIG. 2A, needle end portion 212 is adjacent distal end 114 of port 100 although it may be substantially remote and other means (such as elongated sleeve 300 with or without other devices or mechanisms) may be used to approach, engage, capture and/or provide direct and/or contained passage to or adjacent port distal end 114. In some embodiments, elongated sleeve 300 is readily provided or is telescopically introduced into laparoscopic port lumen 120 and extended to a chosen positioning adjacent needle end portion 212. FIG. 2B shows elongated sleeve 300 fixedly positioned in and across lumen 120 thereby bypassing across seal mechanism 130, while needle end portion 212 is further extended in sleeve lumen 320 in and across port distal end 114 adjacent closed sleeve seal 330.

Figure 2D:
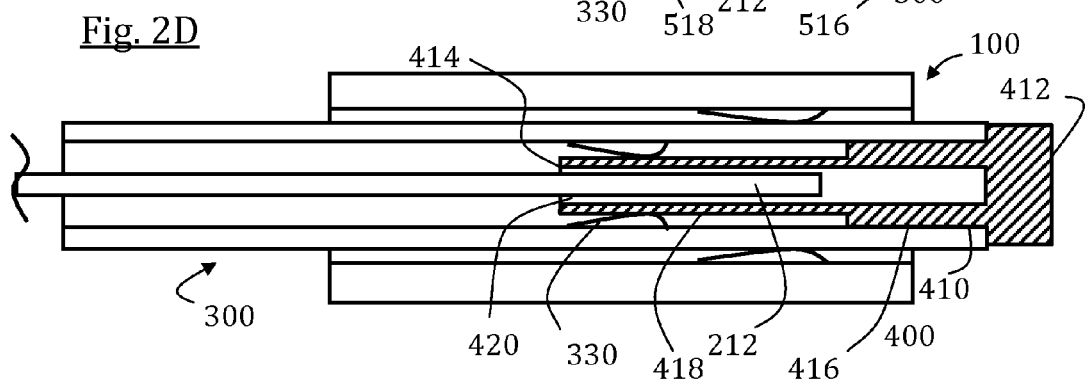
Figure 2E:
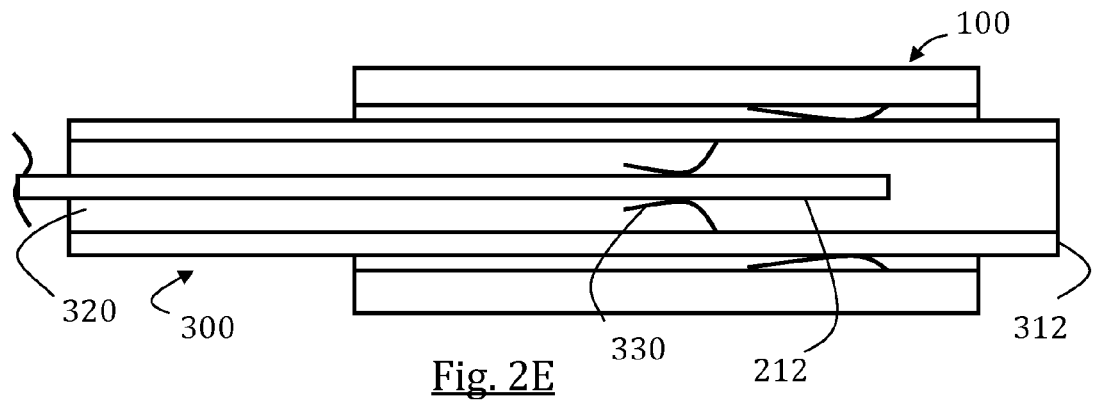

In some embodiments, seal bridge 400 is readily provided or, as shown in FIG. 2D (but also, similarly, in 2C), is next inserted in sleeve lumen 320 while bridging across and/or deactivating the at least one sleeve seal 330. The needle end portion 212 may then be passed via sleeve lumen 320 across the at least one sleeve seal 330. In order to connect an end effector, a surgical head or any other designated head (not shown) to needle end portion 212, the latter may first be extended out in outer environment, therefore the seal bridge should first be removed or uncovered, as shown in FIG. 2E, so it will not disrupt this extension. In some embodiments, seal bridge 400 (or, similarly, seal bridge 500 in FIG. 2C) is manually removed by the medical practitioner, and/or needle 200 itself is used to withdraw the seal bridge by being applied to push it proximally to a complete removal.

Figure 3:
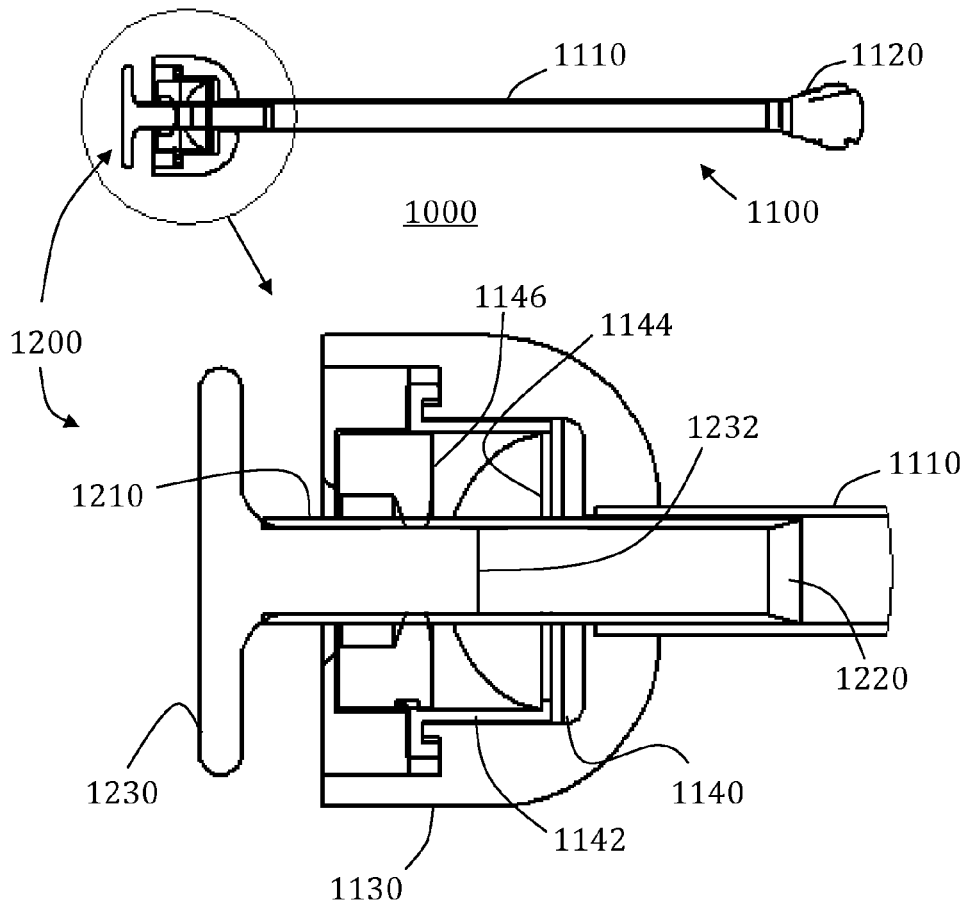
FIG. 3 schematically illustrates a cut view and an enlarged partial view of a laparoscopic inter-sleeve system releasably connected to a seal bridge plug, in accordance with an exemplary embodiment of the present invention.

Reference is now made to FIG. 3 which schematically illustrates a cut view and an enlarged partial view of a system 1000 comprising a laparoscopic inter-sleeve 1100 releasably connected to a seal bridge, such as a seal bridge plug, 1200, in accordance with an exemplary embodiment of the present invention. Inter-sleeve 1100 is telescopically deployable in a laparoscopic port (not shown) which may or may not be a universal or other commercially available port, sized and configured for providing passage to regular sized instruments in diameters of less than 25 mm, optionally less than 15 mm, or optionally of less than 10 mm or of any intermediate value. Inter-sleeve 1100 includes an elongated hollow body 1110 distally connected to a contractible-expandable funnel-like member 1120 meant for improving engagement and/or accommodating entry of slender or other artifacts, such as a needle end portion, into hollow body 1110. Hollow body 1110 is connected at its proximal end to a handle 1130 also serves as a housing for a snapped-in seal mechanism 1140. Seal mechanism 1140 includes a proximal instruments seal 1146 and a distal zero seal 1144 connected with a tubular member 1142 having distal snap-locking means to connect with handle 1130. In some embodiments, instruments seal 1146 is a radially partially slitted flat, cone or dome type seal or an iris-type seal having a minute central opening capable of radially widening at oversized artifacts passing therethrough, while maintaining a sealed periphery thereabout. In some embodiments, distal zero seal 1144 may be a duckbill type seal or any membrane-type seal configured for complete sealing when under a predetermined minimal positive pressure difference between bodily chamber and outer environment and when it is not diverted or forced open, for example by an artifact passing therethrough.

Seal bridge plug 1200 includes a hollow tube portion 1210 air-tightly encompassing at a proximal portion thereof a mating protrusion 1232 of a handheld plug 1230. Plug 1230 may be removable or permanently fixed in tube portion 1210, and optionally and alternatively, plug 1230 and tube portion 1210 are formed as a single part. Distal end 1220 may have internal beveled edges (such as divergently opened) to improve unhindered sliding thereunto of non-concentrically positioned artifacts.

Seal bridge plug 1200 is shown fully deployed in inter-sleeve 1100 lumen in a way that bypasses and bridges across both seals 1144 and 1146; while the distal zero seal 1144 is forced to be opened and deactivated, the proximal instruments seal 1146 is forced to widen its central opening around periphery of tube portion 1210 in an air-tight fashion. As shown in FIG. 3, seal bridge plug 1200 is sized to receive a length of an incoming needle end portion distally away from seals 1144 and 1146. When a needle end portion (not shown) is received and pressed against protrusion 1232 to force seal bridge plug 1200 out, it first emerges through zero seal 1144 and then instruments seal 1146, before tube portion 1210 is completely withdrawn from the seals, so that when such withdrawing happens, a new air-tight relations are accomplished between instruments seal 1146 and periphery of needle free end.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A method for passing an end portion of a needle instrument shaft of a needle system from a body cavity to an outer environment, the system having at least one laparoscopic port defining at least a port lumen between said body cavity and said outer environment, and a seal in said laparoscopic port across said port lumen, comprising:
bridging across and/or deactivating said seal in said port lumen by inserting a seal bridge into said port lumen, through a proximal opening of said laparoscopic port;
passing said end portion of said needle instrument shaft of said needle system from said body cavity into said port lumen via a distal opening of said seal bridge;
positioning a portion of said needle instrument shaft across said seal;
removing said seal bridge.

2. The method according to claim 1, comprising positioning said end portion of said needle instrument shaft across said seal by positioning said end portion of said needle instrument shaft through the distal opening of said seal bridge and into a lumen of said seal bridge.

3. The method according to claim 1, wherein the distal opening of said seal bridge has a beveled entry passage.

4. The method according to claim 1, further comprising telescopically introducing an elongated sleeve in the port lumen of said laparoscopic port through a proximal opening of said laparoscopic port, thereby bypassing said seal of said laparoscopic port, the elongated sleeve having a sleeve lumen with a second seal therein, said seal bridge thereby bridging across and/or deactivating said second seal in said sleeve lumen, the method further comprising extending said elongated sleeve to a chosen position adjacent said end portion of said needle instrument shaft.

5. The method according to claim 1, further comprising connecting an end effector or a surgical head to said end portion of said needle instrument shaft.

6. The method according to claim 1, wherein said seal in said port lumen is a zero seal or an instrument seal.

7. A method for passing an end portion of a needle instrument shaft of a needle system from a body cavity to an outer environment, the system having at least one laparoscopic port defining at least a port lumen between said body cavity and said outer environment, and a seal in said port lumen, comprising:
- bridging across and/or deactivating said seal in said port lumen by inserting a seal bridge into said port lumen, through a proximal opening of said laparoscopic port;
- passing said end portion of said needle instrument shaft of said needle system from said body cavity into said port lumen; and
- positioning a portion of said needle instrument shaft across said seal by pushing said needle instrument shaft on a distal end portion of said seal bridge.

8. The method according to claim 7, further comprising removing said seal bridge.

9. The method according to claim 7, further comprising connecting an end effector or a surgical head to said end portion of said needle instrument shaft.

10. The method according to claim 7, wherein said seal in said port lumen is a zero seal or an instrument seal.

* * * * *